US00PP12035P2

(12) United States Plant Patent
Fruehwirth

(10) Patent No.: US PP12,035 P2
(45) Date of Patent: Aug. 7, 2001

(54) POINSETTIA PLANT NAMED 'ECKADELA'

(75) Inventor: Franz Fruehwirth, Encinitas, CA (US)

(73) Assignee: Paul Ecke Ranch, Inc., Encinitas, CA (US)

( * ) Notice: Subject to any disclaimer, the term of this patent is extended or adjusted under 35 U.S.C. 154(b) by 0 days.

(21) Appl. No.: 09/432,718

(22) Filed: Nov. 2, 1999

(51) Int. Cl.[7] ..... A01H 5/00

(52) U.S. Cl. ..... Plt./307
(58) Field of Search ..... Plt./307

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Poinsettia plant named 'Eckadela', characterized by its bright red bracts; early flowering, response time about 8 weeks; freely flowering; dark green leaves; upright, mounded and very freely branching habit; and excellent postproduction longevity.

2 Drawing Sheets

BACKGROUND OF THE INVENTION

The present invention relates to a new and distinct cultivar of Poinsettia plant, botanically known as *Euphorbia pulcherrima* Willd., and hereinafter referred to by the name 'Eckadela'.

The new Poinsettia is a naturally-occurring mutation of the commercial *Euphorbia pulcherrima* Willd. cultivar Lilo, disclosed in U.S. Plant Pat. No. 6,694. The new Poinsettia was selected by the Inventor in a greenhouse in Encinitas, Calif., in 1988. The objective of the Inventor's Poinsettia development program is to create new Poinsettia cultivars having interesting bract and leaf display, color and form; strong and freely branching stems; and good post-production longevity.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eckadela'. These characteristics in combination distinguish 'Eckadela' as a new and distinct cultivar:

1. Bright red bracts.
2. Early flowering, response time about 8 weeks.
3. Freely flowering.
4. Dark green leaves.
5. Upright and mounded plant habit.
6. Very freely branching habit.
7. Excellent postproduction longevity.

In side-by-side comparisons conducted in Encinitas, Calif., plants of the new Poinsettia differed from plants of the parent cultivar, Lilo, in the following characteristics:

1. Plants of the new Poinsettia are more freely and more uniformly branching than plants of 'Lilo'.

2. Plants of the new Poinsettia are more compact than plants of 'Lilo'.

3. Plants of the new Poinsettia flower about five to seven days earlier than plants of 'Lilo'.

BRIEF DESCRIPTION OF THE PHOTOGRAPHS

The accompanying colored photographs illustrate the overall appearance of the new Poinsettia, showing the colors as true as it is reasonably possible to obtain in colored reproductions of this type.

The photograph at the top of the first sheet comprises a side perspective view of a typical plant of 'Eckadela'.

The photograph at the bottom top of the first sheet comprises a top perspective view of a typical plant of 'Eckadela'.

The photograph on the second sheet is a close-up views of typical bracts and leaves of 'Eckadela' (left) and 'Lilo' (right). Bract and foliage colors in the photographs may differ from actual colors due to light reflectance.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The photographs and the following observations and measurements describe 16 week old plants grown in Encinitas, Calif., under commercial practice in a glass-covered greenhouse with day temperatures ranging from 21 to 27° C., night temperatures ranging from 18 to 20° C., and light levels about 4,000 foot-candles. Plants were grown in 16-cm pots, pinched one time, and flowered under naturally lengthening nyctoperiods during the fall/early winter.

In the following description, color references are made to The Royal Horticultural Society Colour Chart except where general terms of ordinary dictionary significance are used.

Botanical classification: *Euphorbia pulcherrima* Willd. 'Eckadela'.

Parentage: Naturally-occurring mutation of *Euphorbia pulcherrima* Willd. cultivar Lilo, disclosed in U.S. Plant Pat. No. 6,694.

Propagation:

*Type cutting.*—Terminal cuttings.

*Time to initiate roots.*—Summer: About 12 to 18 days at 27° C. Winter: About 15 to 18 days at 24° C.

*Time to develop roots.*—Summer: About 26 days at 27° C. Winter: About 26 days at 24° C.

*Rooting habit.*—Freely branching, becoming fibrous with development.

Plant description:

*Plant form.*—Inverted triangle.

*Growth habit.*—Upright and mounded. Very freely branching. Branching is enhanced by removing the shoot apex. Moderately vigorous.

*Plant height.*—About 30 cm.

*Plant spread.*—53 cm.

*Crop time.*—From unrooted cuttings to a flowering plant in a 16-cm container, about 16 weeks are required.

*Stem description.*—Strong stems. Number of lateral branches: About eight lateral branches are formed after removal of the terminal apex. Lateral branch length: About 25 cm. Internode length: About 1.5 cm. Stem color: 146A to 146B.

*Foliage description.*—Arrangement: Alternate. Quantity of leaves per lateral branch: About 12. Length: About 11 cm. Width: About 8 cm. Shape: Mostly ovate or lobed. Apex: Acuminate. Base: Acute. Margin: Entire. Texture: Smooth, dull; very sparse pubescence on lower surface. Color: Young foliage, upper surface: 147A. Young foliage, lower surface: 147B. Mature foliage, upper surface: Darker than 139A. Mature foliage, lower surface: 139A. Venation, upper surface: 139A. Venation, lower surface: 139C. Petiole: Length: About 7 cm. Diameter: About 2 mm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions. Response time is about 8 weeks.

*Quantity of inflorescences.*—One per lateral branch, usually about eight per plant.

*Inflorescence size.*—Diameter: About 27 cm. Height (depth): About 4 cm.

*Flower bracts.*—Quantity of flower bracts per inflorescence: Usually about 10 primary bracts and about 8 smaller secondary bracts per inflorescence. Length, largest bracts: About 13 cm. Width, largest bracts: About 9.5 cm. Shape: Mostly ovate. Apex: Acuminate. Base: Acute. Margin: Entire. Texture: Smooth. Aspect: Mostly horizontal. Color: Developing, upper surface: 45B. Developing, lower surface: 45C. Mature, upper surface: 45A. Mature, lower surface: 46B.

*Cyathia.*—Quantity: Usually about 15 per corymb. Diameter of cyathia cluster: About 3.5 by 4 cm. Length: About 1 cm. Width: About 5 mm. Color: Immature: 144A. Mature: 144B. Peduncle: Length: About 4 mm. Aspect: Strong, erect. Color: 146B. Stamens: Stamen number: Five to ten with numerous stamenoids per cyathium. Anther length: About 1 mm. Anther shape: Oval. Anther color: 46A. Amount of pollen: Scarce to moderate. Pollen color: 14A. Pistils: No pistillate flowers observed. Nectary color: 14A.

Disease resistance: Plants of the new Poinsettia have been observed to be resistant to Botrytis.

Postproduction longevity: Excellent; generally plants maintain good substance and bract color for about eight weeks under interior conditions.

It is claimed:

1. A new and distinct cultivar of Poinsettia plant named 'Eckadela', as illustrated and described.

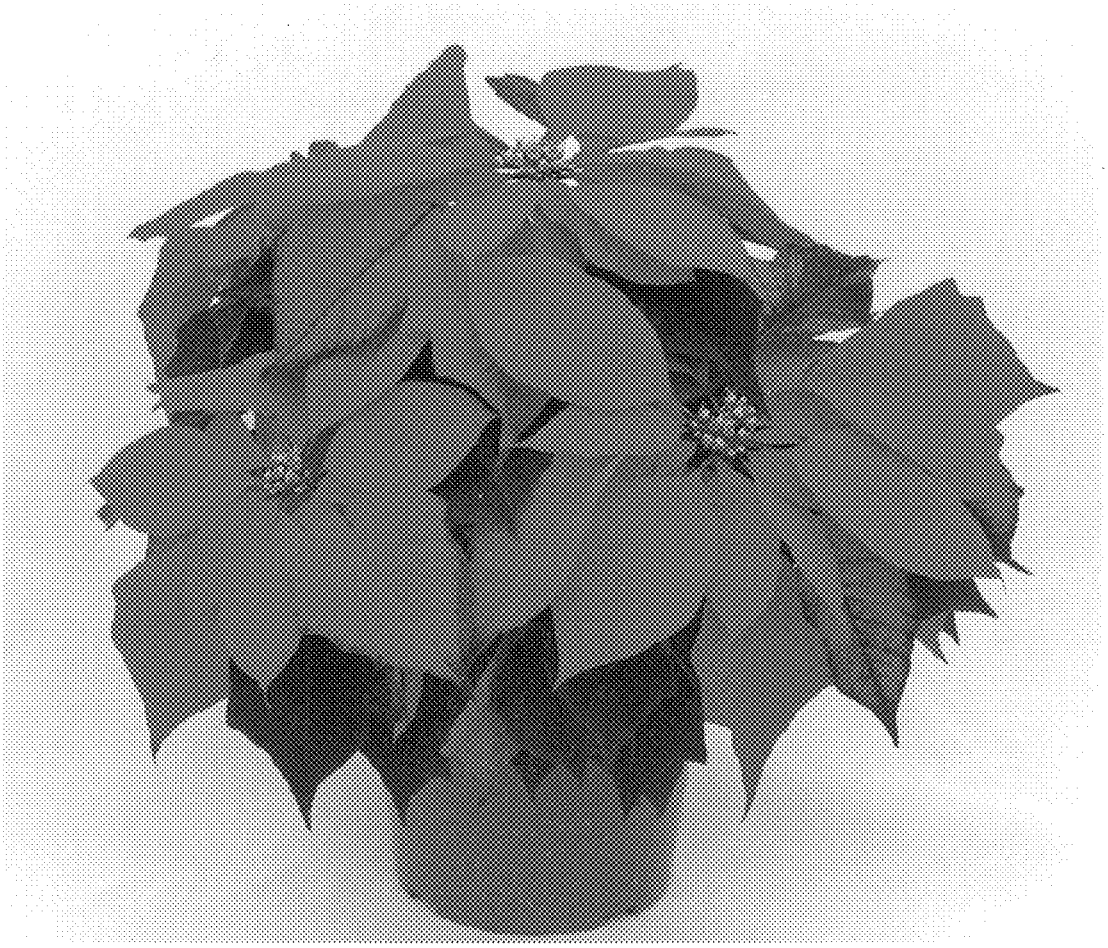
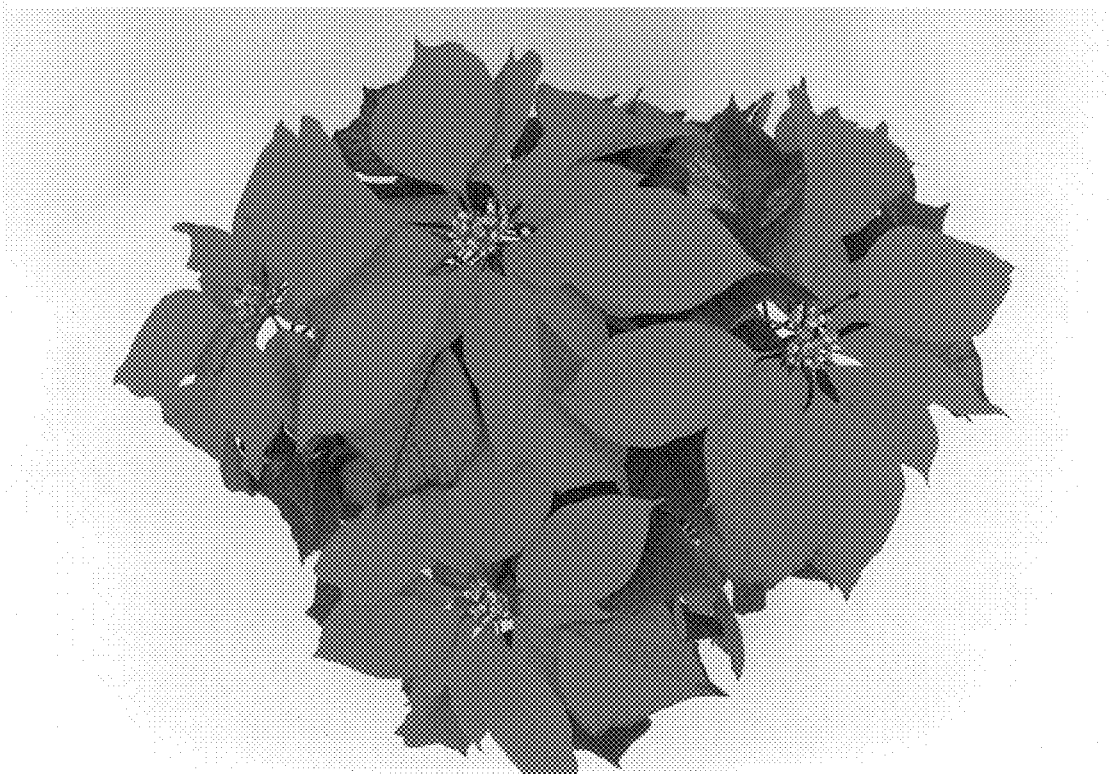

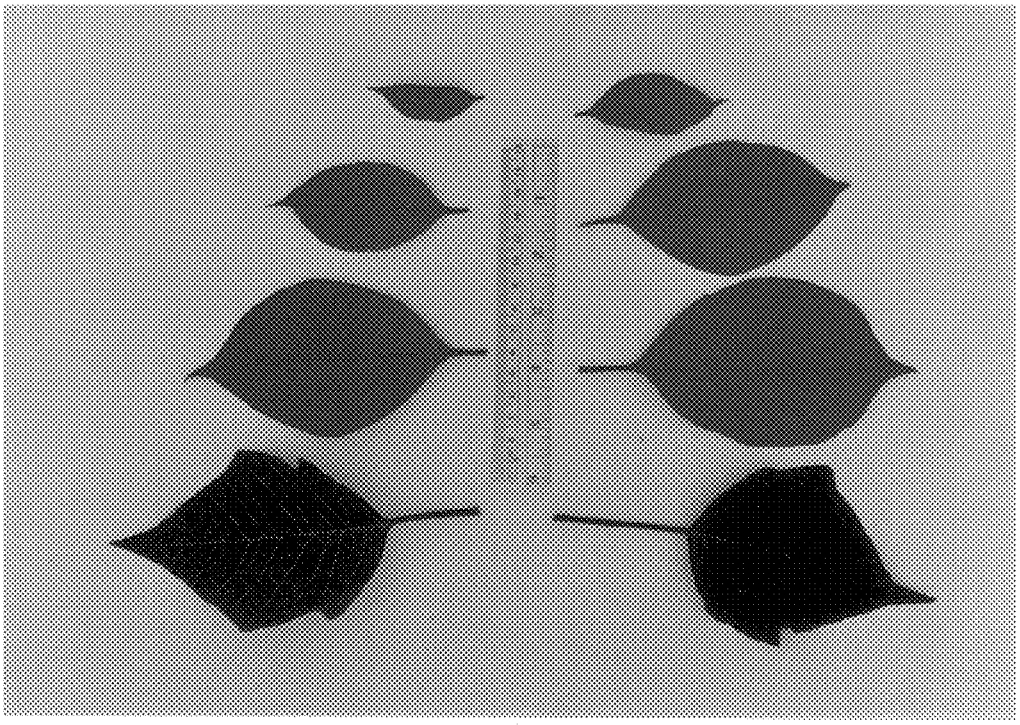

* * * * *